United States Patent
Park et al.

(10) Patent No.: US 10,314,629 B2
(45) Date of Patent: Jun. 11, 2019

(54) FIXING PIN FOR ORTHOPEDIC SURGERY ENABLING INTERNAL FIXATION

(71) Applicant: KYUNGPOOK NATIONAL UNIVERSITY INDUSTRY-ACADEMIC COOPERATION FOUNDATION, Daegu (KR)

(72) Inventors: Ilhyung Park, Daegu (KR); Chang-Wug Oh, Daegu (KR); Chul-woo Park, Daegu (KR); Sanghyun Joung, Daegu (KR); Hyunjoo Lee, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 175 days.

(21) Appl. No.: 15/316,750

(22) PCT Filed: Jun. 12, 2015

(86) PCT No.: PCT/KR2015/005928
§ 371 (c)(1),
(2) Date: Dec. 6, 2016

(87) PCT Pub. No.: WO2015/190861
PCT Pub. Date: Dec. 17, 2015

(65) Prior Publication Data
US 2017/0143395 A1    May 25, 2017

(30) Foreign Application Priority Data

Jun. 13, 2014   (KR) .................. 10-2014-0072246

(51) Int. Cl.
A61B 17/84         (2006.01)
A61B 17/88         (2006.01)
(Continued)

(52) U.S. Cl.
CPC .......... *A61B 17/846* (2013.01); *A61B 17/683* (2013.01); *A61B 17/8872* (2013.01); *A61B 17/8685* (2013.01); *A61B 2090/034* (2016.02)

(58) Field of Classification Search
CPC ....... A61B 17/84; A61B 17/846; A61B 17/88; A61B 17/8872
See application file for complete search history.

(56) References Cited

U.S. PATENT DOCUMENTS 3,351,054 A * 11/1967 Florek ............... A61B 17/1686
                                                                606/104
4,790,304 A * 12/1988 Rosenberg ......... A61B 17/7266
                                                                606/302

(Continued)

FOREIGN PATENT DOCUMENTS

EP          2740427 A1    6/2014
EP          2740428 A1    6/2014
(Continued)

OTHER PUBLICATIONS

International Search Report dated Jul. 31, 2015 for PCT application No. PCT/KR2015/005928.

*Primary Examiner* — Christopher J Beccia
(74) *Attorney, Agent, or Firm* — Ohlandt, Greeley, Ruggiero & Perle, L.L.P.

(57) ABSTRACT

A fixing pin for orthopedic surgery is provided. The fixing pin for orthopedic surgery includes: an inner fixing pin inserted from one-side cortex of a bone to the opposite-side cortex thereof; an outer fixing pin including a first hole and a first screw portion formed to protrude from a front end thereof, the first hole being penetrated by the inner fixing pin (Continued)

so that front and rear ends of the inner fixing pin protrude, the outer fixing pin being inserted into only one-side cortex of the bone, and the inner fixing pin being fixed to the outer fixing pin; and a sleeve including a second hole and fixed to the outer fixing pin, the second hole being penetrated by the outer fixing pin so that front and rear ends of the outer fixing pin protrude. Therefore, according to the present disclosure, it is possible to perform internal fixation even after reposition of bone fracture has been performed using a fixing pin.

9 Claims, 25 Drawing Sheets

(51) Int. Cl.
*A61B 17/68* (2006.01)
*A61B 17/86* (2006.01)
*A61B 90/00* (2016.01)

(56) References Cited

U.S. PATENT DOCUMENTS

| | | | | |
|---|---|---|---|---|
| 7,326,211 | B2* | 2/2008 | Padget | A61B 17/88 606/67 |
| 7,794,452 | B2* | 9/2010 | Ferguson | A61B 17/1735 606/1 |
| 2009/0318981 | A1 | 12/2009 | Kang | |
| 2012/0010619 | A1* | 1/2012 | Barsoum | A61B 17/8897 606/79 |

FOREIGN PATENT DOCUMENTS

| | | |
|---|---|---|
| JP | H06125918 A | 5/1994 |
| JP | 2009505748 A | 2/2009 |
| KR | 20030017505 A | 3/2003 |
| KR | 100872530 A | 12/2008 |
| KR | 20090133060 A | 12/2009 |
| WO | 2001080751 A1 | 11/2001 |
| WO | 2004025132 A2 | 3/2007 |

* cited by examiner

FIXING PIN FOR ORTHOPEDIC SURGERY ENABLING INTERNAL FIXATION

CROSS-REFERENCE TO RELATED APPLICATIONS

This application claims priority from Korean Patent Application No. 10-2014-0072246, filed on Jun. 13, 2014, in the Korean Intellectual Property Office, the disclosure of which is incorporated herein by reference in its entirety.

BACKGROUND OF THE INVENTION

Field of the Invention

Apparatuses and methods consistent with the present disclosure relate to a fixing pin for orthopedic surgery, and more particularly, to a fixing pin for orthopedic surgery for performing reposition of bone fracture using the fixing pin.

Description of the Related Art

There is a method of inserting a fixing pin into each bone fragment to move the bone fragment for accurate reposition of a fractured bone. At the time of inserting the fixing pin as described above, a single fixing pin is used, and in order to increase fixation force, generally, a method of penetrating both side cortexes of the bone is used. However, in this case, it is not easy to perform internal fixation using a metal nail due to the fixing pin passing through the bone marrow cavity.

To this end, in the case of a fixing pin according to the related art, a method of inserting the fixing pin at a site deviated from the center of the bone, or a method of removing the fixing pin after reposition and performing internal fixation has been used.

However, since it was impossible to obtain strong fixation force in these methods, it was difficult to perform accurate reposition of bone fracture, and an incision site was wide, such that it was impossible to prevent secondary infection in a surgical site. Further, a surgical method was not easy, such that in the case in which a surgeon is not trained in surgical know-how, secondary bone fracture or secondary damage in the vicinity of the surgical site may occur.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above.

The present disclosure provides a fixing pin for orthopedic surgery capable of solving a problem that it is impossible to perform internal fixation in the case of performing reposition of bone fracture using a fixing pin, and capable of improving accuracy and safety of musculoskeletal reconstruction surgery of damaged upper and lower extremities.

According to an aspect of the present disclosure, a fixing pin for orthopedic surgery includes: an inner fixing pin inserted from one-side cortex of a bone to the opposite-side cortex thereof; and an outer fixing pin including a first hole and a first screw portion formed to protrude from a front end thereof, the first hole being penetrated by the inner fixing pin so that front and rear ends of the inner fixing pin protrude, the outer fixing pin being inserted into only one-side cortex of the bone, and the inner fixing pin being fixed to the outer fixing pin.

The fixing pin for orthopedic surgery may further include a sleeve including a second hole, wherein the second hole is penetrated by the outer fixing pin so that front and rear ends of the outer fixing pin protrude, and the sleeve is fixed to the outer fixing pin.

The fixing pin for orthopedic surgery may further include a fixing nut fixing the sleeve to the outer fixing pin.

The fixing nut may be screw-coupled to a second screw portion formed at a middle portion of the outer fixing pin to fix the sleeve so that the sleeve is not separated from the outer fixing pin.

The fixing pin for orthopedic surgery may further include a stopper fixing the inner fixing pin to the outer fixing pin.

The stopper may include a first coupling groove and a first coupling protrusion, wherein the first coupling groove is coupled to a second coupling protrusion of the inner fixing pin, and the first coupling protrusion is coupled to a second coupling groove of the outer fixing pin.

The sleeve may include a plurality of spikes having at least one shape of a corn, a triangular pyramid, and a quadrangular pyramid at a front end thereof.

A spike may be formed to continuously protrude from a front end of the sleeve.

The sleeve may include a washer inserted on the front end thereof, wherein the washer includes a plurality of spikes having at least one shape of a corn, a triangular pyramid, and a quadrangular pyramid on one surface thereof.

The sleeve may include a washer inserted on the front end thereof, wherein the washer includes a spike formed to continuously protrude from a front end of the washer.

The fixing pin for orthopedic surgery may further include a spacer disposed between the inner fixing pin and the outer fixing pin in order to insert the inner fixing pin at an accurate position, and including a hole penetrated by the inner fixing pin.

According to another aspect of the present disclosure, a fixing pin for orthopedic surgery includes: an inner fixing pin inserted from one-side cortex of a bone to the opposite-side cortex thereof; an outer fixing pin including a first hole and a first screw portion formed to protrude from a front end thereof, the first hole being penetrated by the inner fixing pin so that front and rear ends of the inner fixing pin protrude, the outer fixing pin being inserted into only one-side cortex of the bone, and the inner fixing pin being fixed to the outer fixing pin; a sleeve including a second hole and fixed to the outer fixing pin, the second hole being penetrated by the outer fixing pin so that front and rear ends of the outer fixing pin protrude; a fixing nut fixing the sleeve to the outer fixing pin; and a stopper fixing the inner fixing pin to the outer fixing pin.

According to exemplary embodiments of the present disclosure, the fixing pin for orthopedic surgery having the structure as described above may prevent secondary bone fracture caused by insertion and distraction of the fixing pin due to strong fixation force between the fixing pin and the bone at the time of reposition of bone fracture, and facilitate reposition of bone fracture.

Further, according to the exemplary embodiments of the present disclosure, the fixing pin for orthopedic surgery may minimize incision of a surgical site at the time of inserting the fixing pin to thereby prevent secondary infection of the surgical site, which is advantageous in rapid recovery of the surgical site.

In addition, according to the exemplary embodiments of the present disclosure, since the fixing pin for orthopedic surgery may be separated into the inner fixing pin and the outer fixing pin, after reposition of bone fracture, only the inner fixing pin is removed, thereby making it possible to perform internal fixation.

Furthermore, since the fixing pin for orthopedic surgery has a shape and a configuration capable of being applied at the time of treating bone fracture using a robot, the fixing pin for orthopedic surgery may be used in treating bone fracture using the robot in the future.

BRIEF DESCRIPTION OF THE DRAWING FIGURES

The above and/or other aspects of the present invention will be more apparent by describing certain exemplary embodiments of the present invention with reference to the accompanying drawings, in which.

DETAILED DESCRIPTION OF THE EXEMPLARY EMBODIMENTS

Hereinafter, a fixing pin for orthopedic surgery according to an exemplary embodiment of the present disclosure will be described with reference to the accompanying drawings. However, if it is determined that the detailed description of relevant known functions or components makes subject matters of the present disclosure obscure, the detailed description and drawing thereof will be omitted.

Figure 1:
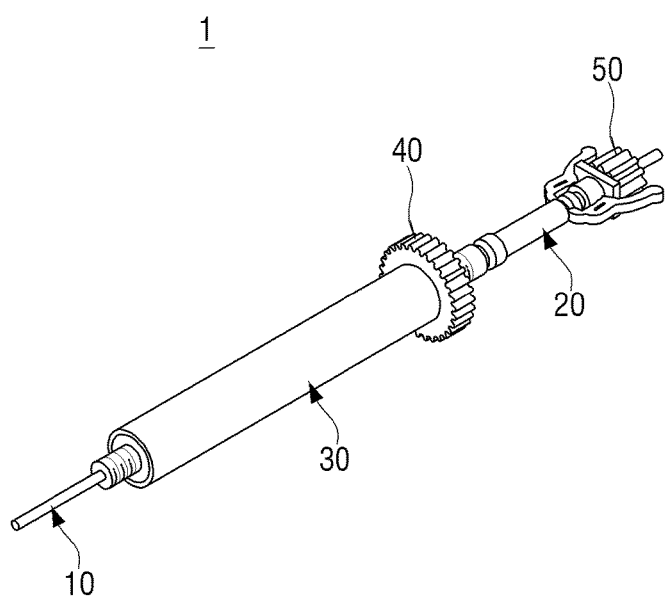
FIG. 1 is a perspective view illustrating a fixing pin for orthopedic surgery according to an exemplary embodiment of the present disclosure.
Figure 2:
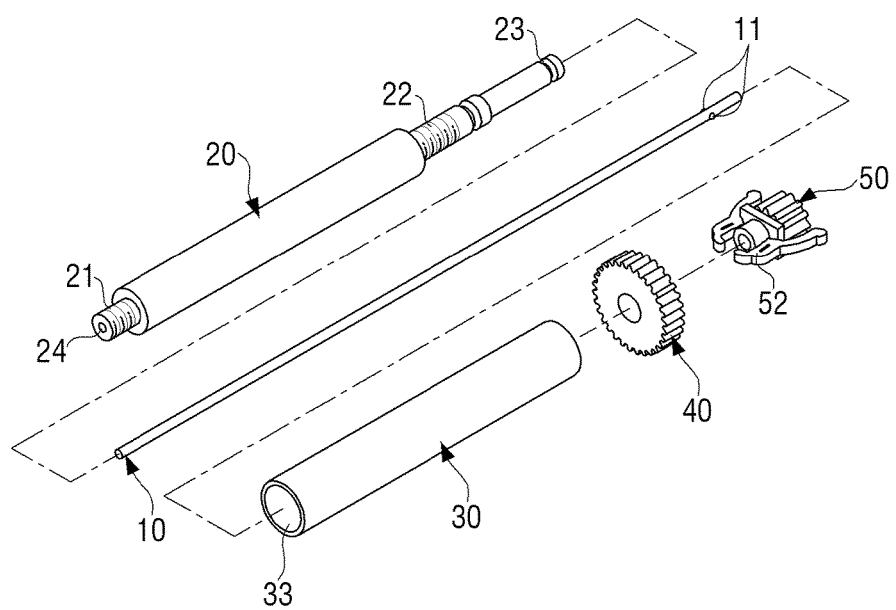
FIG. 2 is an exploded perspective view of the fixing pin of FIG. 1.
Figure 3:
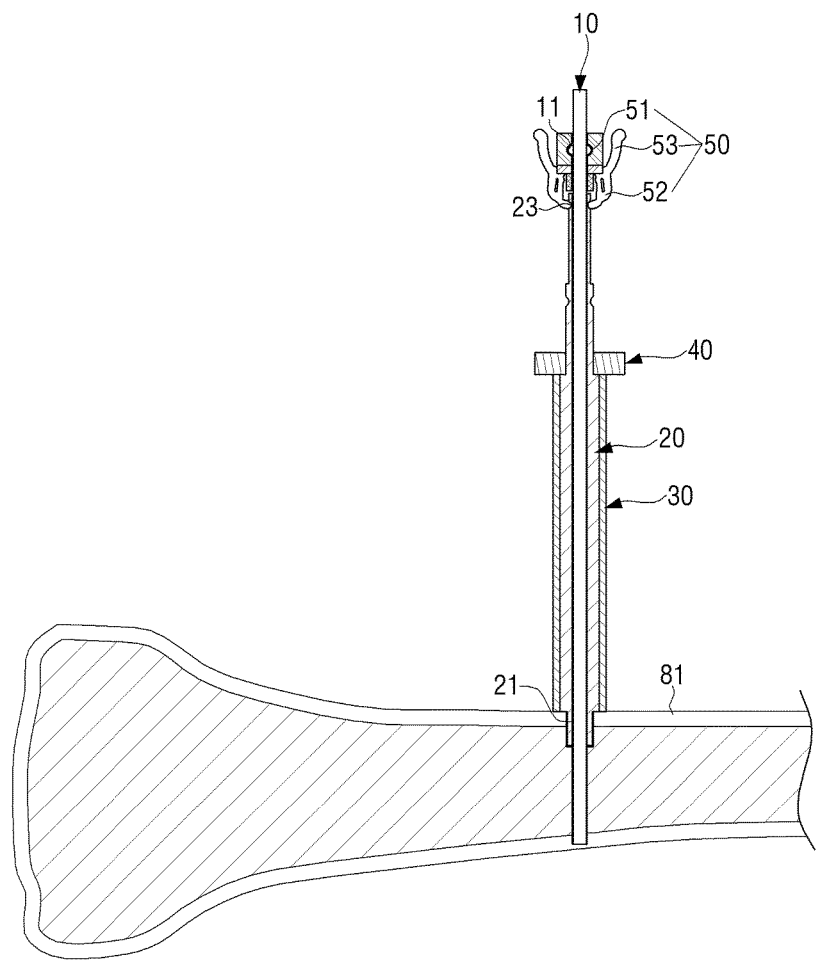
FIG. 3 is a cross-sectional view of the fixing pin of FIG. 1.

Referring to FIGS. 1 to 3, a fixing pin 1 for orthopedic surgery according to an exemplary embodiment of the present disclosure includes an inner fixing pin 10, an outer fixing pin 20, and a sleeve 30.

The inner fixing pin 10 has a long bar shape, preferably, a cylindrical shape. A material of the inner fixing pin 10 may be stainless steel or titanium. Since the inner fixing pin 10 is assembled so that the inner fixing pin 10 penetrates through the inside of the outer fixing pin 20 and both front and rear ends thereof protrude, it is preferable that the inner fixing pin 10 has a length longer than that of the outer fixing pin 20.

A second coupling protrusion 11 is formed at a rear end portion of the inner fixing pin 10, and is coupled to a first coupling groove 51 of a stopper 50 to be described below, thereby adjusting a penetration depth of the inner fixing pin in the bone while fixing the inner fixing pin 10 to the outer fixing pin 20. The number of provided second coupling protrusions is at least two or more.

A shape of the outer fixing pin 20 is a long bar including a first hole 24 penetrated by the inner fixing pin 10. Preferably, the shape of the outer fixing pin 20 is a hollow cylinder. A material of the outer fixing pin 20 may also be stainless steel or titanium. Since the outer fixing pin 20 is assembled so that the outer fixing pin penetrates through the inside of the sleeve and both front and rear ends thereof protrude, it is preferable that a length of the outer fixing pin 20 is shorter than that of the inner fixing pin 10 but longer than that of the sleeve 30.

The outer fixing pin 20 includes a first screw portion 21 at the front end, and the first screw portion 21 is screw-coupled to one-side cortex 81 when the outer fixing pin 20 is inserted.

The outer fixing pin 20 includes a second screw portion 22 at a middle portion thereof, and the second screw portion 22 is a portion to which a fixing nut 40 to be described below is screw-coupled in order to fix the sleeve 30 to the outer fixing pin 20. The fixing nut 40 is screw-coupled to the second screw portion 22 of the outer fixing pin 20 to press the sleeve 30, such that the sleeve 30 has strong fixation force by friction with an outer portion of the bone.

The outer fixing pin 20 includes a second coupling groove 23 at the rear end. The second coupling groove 23 is coupled to a first coupling protrusion 52 of a stopper 50 to be described below to fix the outer fixing pin 20 and the inner fixing pin 10.

The inner fixing pin 10 and the outer fixing pin 20 according to the present disclosure are configured to be separated from each other as a double fixing pin structure. This structure may enable internal fixation after reposition of bone fracture.

The fixing pin 1 may further include the sleeve 30 outside the outer fixing pin 20. A shape of the sleeve 30 is a long bar including a second hole 33 penetrated by the outer fixing pin 20. Preferably, the shape of the sleeve is a hollow cylinder. A material of the sleeve 30 may also be stainless steel or titanium. Since the sleeve 30 is assembled so that the outer fixing pin 20 penetrates therethrough and thus both front and rear ends of the outer fixing pin 20 protrude, it is preferable that the sleeve 30 has a length shorter than that of the outer fixing pin 20.

The sleeve 30 allows the fixing pin 1 to have strong fixation force, and has a thickness of 10 mm or so in order to prevent a bending phenomenon of the fixing pin 1 at the time of reposition of bone fracture. Therefore, it is possible to more accurately and easily perform reposition of bone fracture.

The fixing nut 40, which is a member for fixing the sleeve 30 to the outer fixing pin 20, is screw-coupled to the second screw portion 22 formed at the middle portion of the outer fixing pin 20. When the fixing nut 40 is screwed on the outer fixing pin 20, the fixing nut 40 presses the sleeve 30 in a direction toward the bone, thereby generating strong fixation force. There is an exemplary embodiment in which a protrusion portion is formed or a washer 60 is used at the front end of the sleeve 30 in order to further increase the fixation force as described above, but the exemplary embodiment will be described below. Preferably, a material of the fixing nut 40 may also be stainless steel or titanium.

The stopper 50, which is a member fixing the inner fixing pin 10 and the outer fixing pin 20 and adjusting a depth of the inner fixing pin 10 when the inner fixing pin 10 penetrates through the cortex, includes the first coupling groove 51 and the first coupling protrusion 52.

The first coupling groove 51 is coupled to the second coupling protrusion 11 of the inner fixing pin 10, and the number of provided first coupling grooves 51 is at least two or more so as to correspond to the number of second coupling protrusions.

The first coupling protrusion 52 is coupled to the second coupling groove 23 of the outer fixing pin 20, and the number of provided first coupling protrusions 52 is at least two or more. The first coupling protrusion 52 includes a switch portion 53, and the stopper 50 may be coupled or separated by operating the switch portion 53 using a finger.

Figure 4:
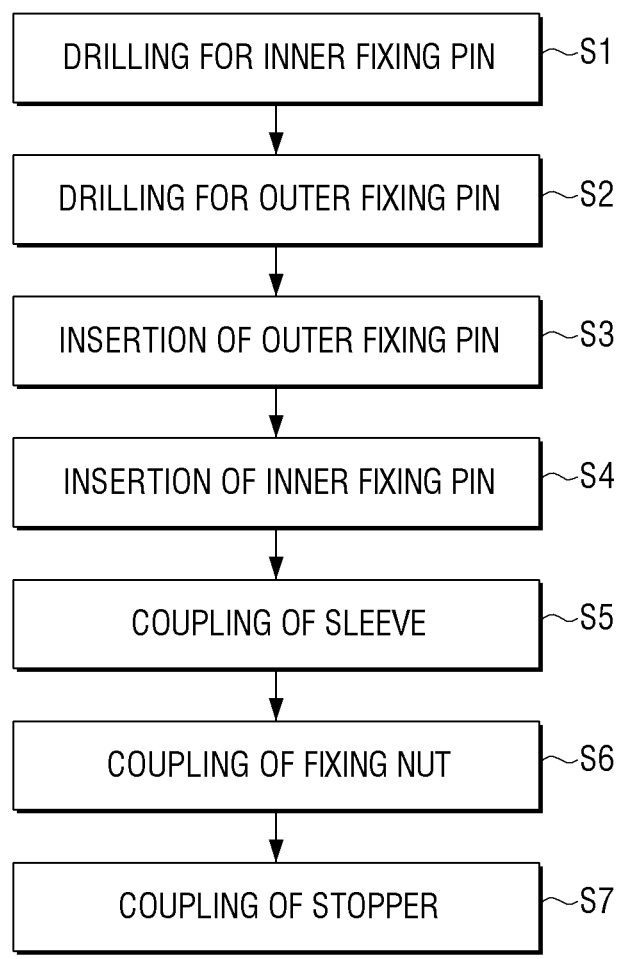
FIG. 4 is a flow chart illustrating an example of a method of using the fixing pin of FIG. 1.

Hereinafter, a method of using the fixing pin for orthopedic surgery according to the exemplary embodiment of the present disclosure described above will be described with reference to a flow chart of FIG. 4 and sequence views of FIGS. 5A to 5G.

Figure 5A:
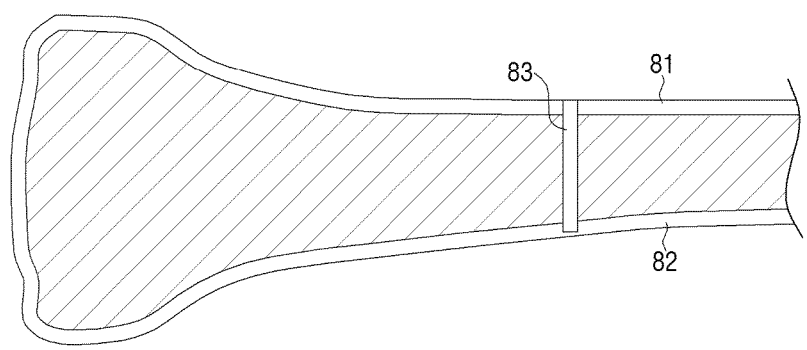
FIGS. 5A to 5G are sequence views illustrating the example of the method of using the fixing pin of FIG. 1.

First, as illustrated in FIG. 5A, drilling for inserting the inner fixing pin 10 is performed (S1). Since the inner fixing pin 10 needs to penetrate up to the opposite-side cortex 82, the drilling is performed from one-side cortex 81 to the opposite-side cortex 82, thereby forming a hole 83 into which the inner fixing pin 10 will be inserted.

Figure 5B:
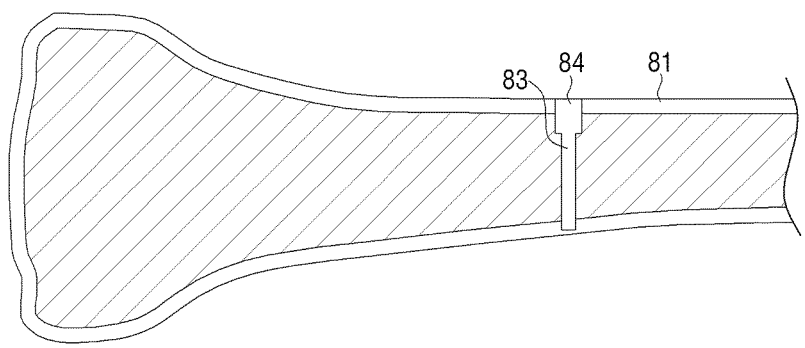

Then, as illustrated in FIG. 5B, drilling for inserting the outer fixing pin 20 is performed (S2). Since the outer fixing pin 20 is inserted into only one-side cortex 81, the drilling is performed only on one-side cortex 81, thereby forming a hole 84 into which the outer fixing pin 20 will be inserted. It is preferable that the drilling is performed so as to form a screw thread in the cortex for coupling with the second screw portion 22 of the outer fixing pin 20. Further, it is preferable that the hole 84 into which the outer fixing pin 20 will be inserted has a size larger than that of the hole 83 into which the inner fixing pin 10 will be inserted.

Figure 5C:
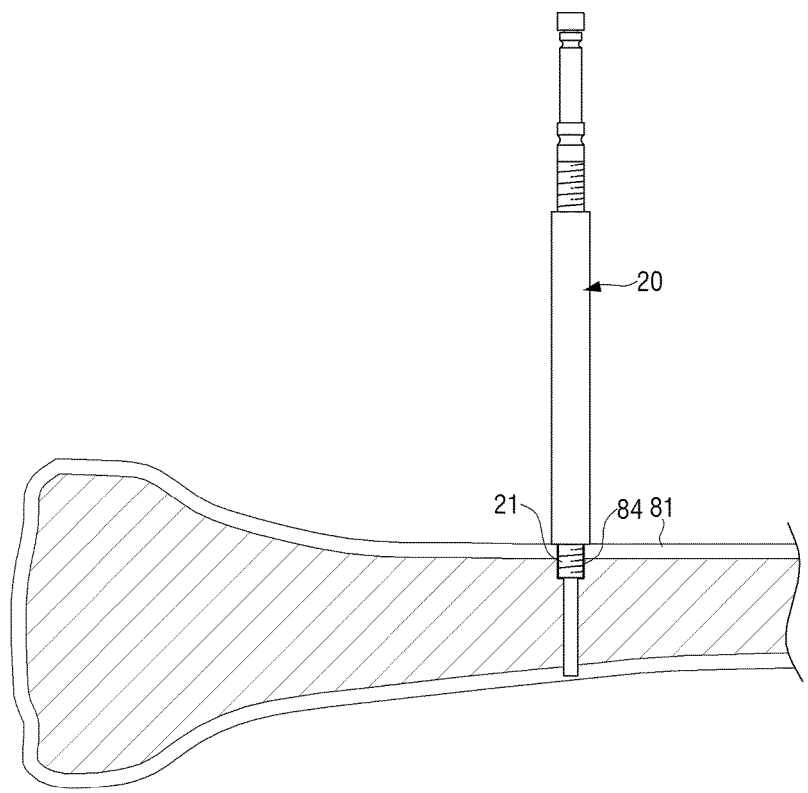

Next, as illustrated in FIG. 5C, the outer fixing pin 20 is inserted into the hole 84 for inserting the outer fixing pin 20, formed in one-side cortex 81 (S3). The outer fixing pin 20 is screw-coupled to the hole 84 for inserting the outer fixing pin 20, formed in one-side cortex along the first screw portion 21 formed at the front end thereof.

Figure 5D:
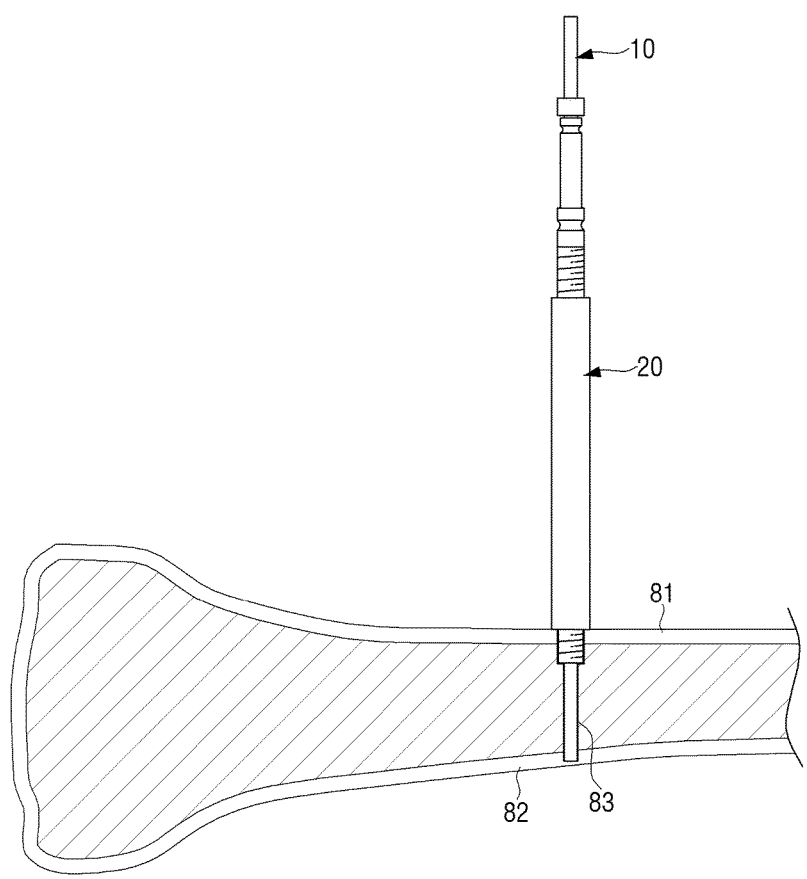

Then, as illustrated in FIG. 5D, the inner fixing pin 10 is inserted into the hole 83 for inserting the inner fixing pin 10 (S4). The inner fixing pin 10 penetrates through the outer fixing pin 20 to thereby be inserted up to the opposite-side cortex 82.

Figure 5E:
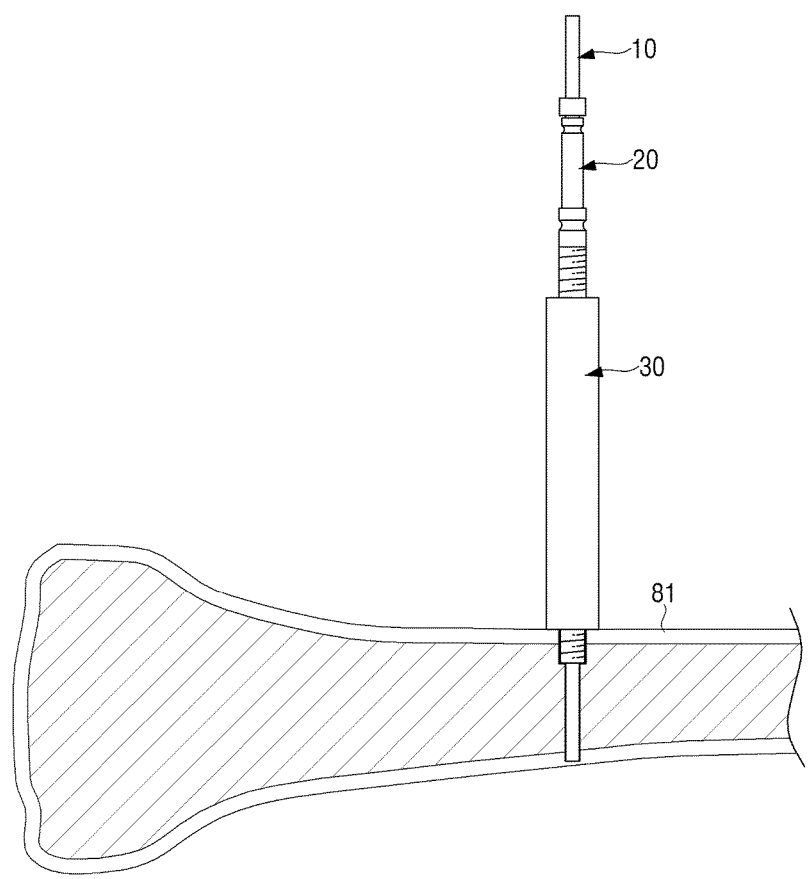
Figure 5F:
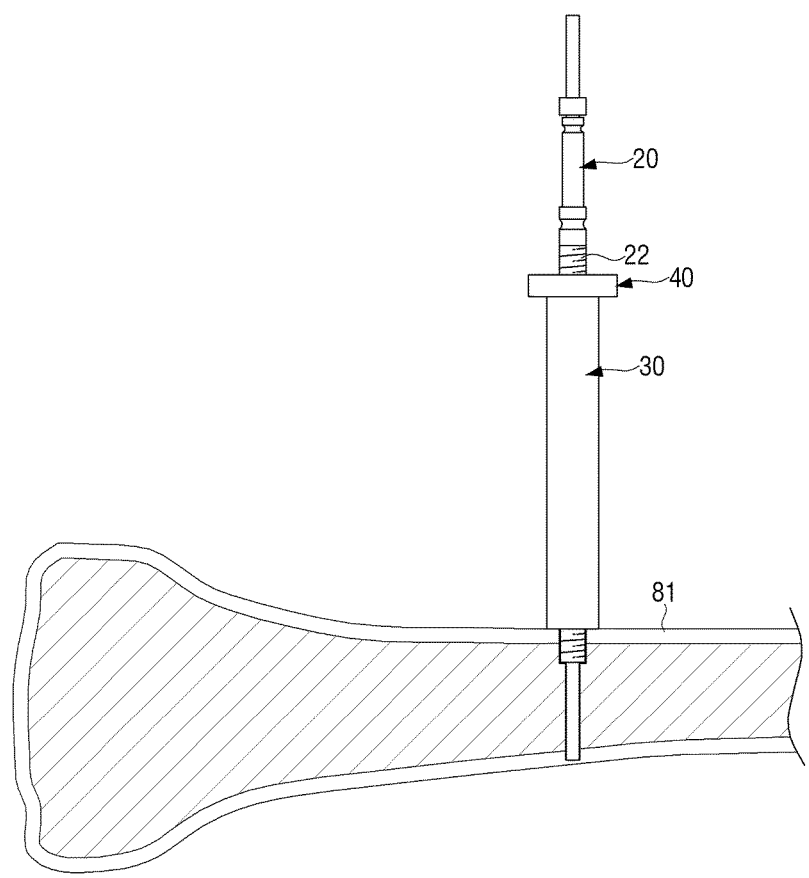

When insertion of the inner fixing pin 10 and the outer fixing pin 20 is completed, subsequently, the sleeve 30 is coupled to the outer portion of the outer fixing pin 20 (S5), as illustrated in FIG. 5E. In this case, the front end of the sleeve contacts one-side cortex 81 of the bone. Then, as illustrated in FIG. 5F, the fixing nut 40 is coupled to the second screw portion 22 formed at the middle portion of the outer fixing pin 20 to press the sleeve 30 toward one-side cortex 81, thereby allowing the sleeve 30 to be firmly fixed to the bone (S6).

Figure 5G:
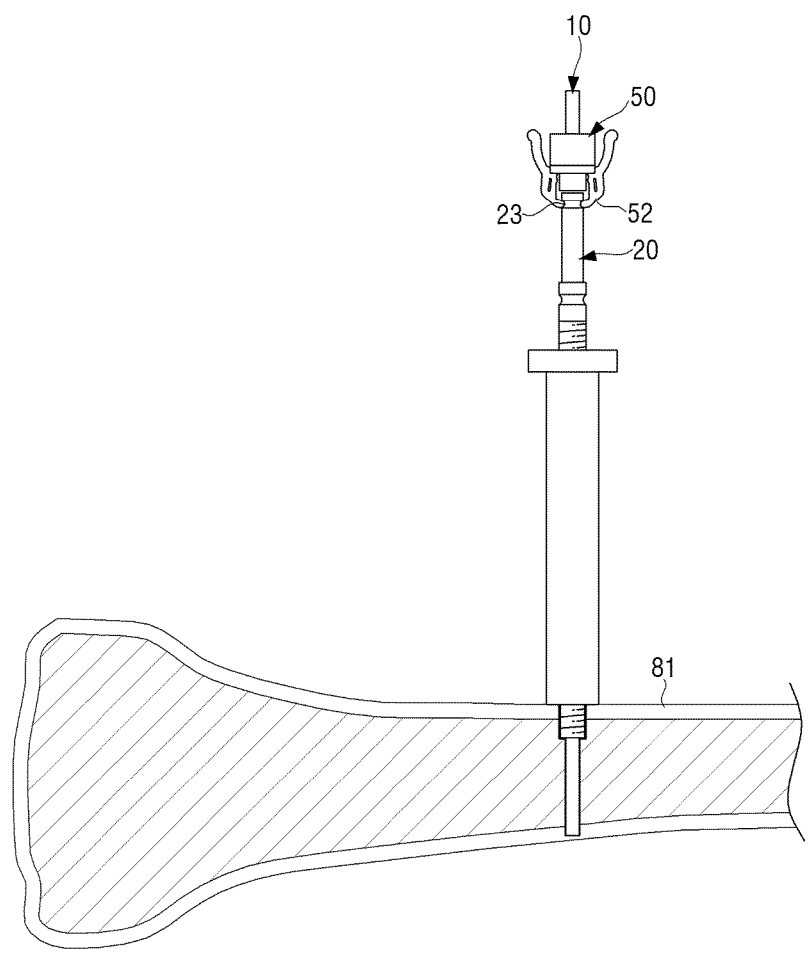

Then, referring to FIGS. 5G and 3, the first coupling groove 51 of the stopper 50 is coupled to the second coupling protrusion 11 of the inner fixing pin 10, and the first coupling protrusion of the stopper 50 is coupled to the second coupling groove 23 of the outer fixing pin 20, thereby fixing the outer fixing pin 20 and the inner fixing pin 10 to each other (S7). The stopper 50 serves to fix the inner fixing pin 10 so as not to be inserted into a deeper portion or separated.

Next, after the fixing pin 1 for orthopedic surgery is firmly fixed to the bone, a method of treating bone fracture using the fixing pin 1 for orthopedic surgery is performed.

For accurate reposition of the fractured bone, the fixing pin 1 for orthopedic surgery is inserted into each bone fragment, thereby performing reposition of the bone. After reposition of the fractured bone, in order to perform internal fixation using a metal nail, the inner fixing pin 10 is removed. In this case, as the inner fixing pin 10 penetrating through both side cortexes 81 and 82 is removed, the metal nail (implant) may be inserted into the bone marrow cavity. After the inner fixing pin 10 is removed, the metal nail (implant) is inserted and fixed. Thereafter, when the outer fixing pin 20 is removed, bone fracture treatment is terminated.

Figure 6:
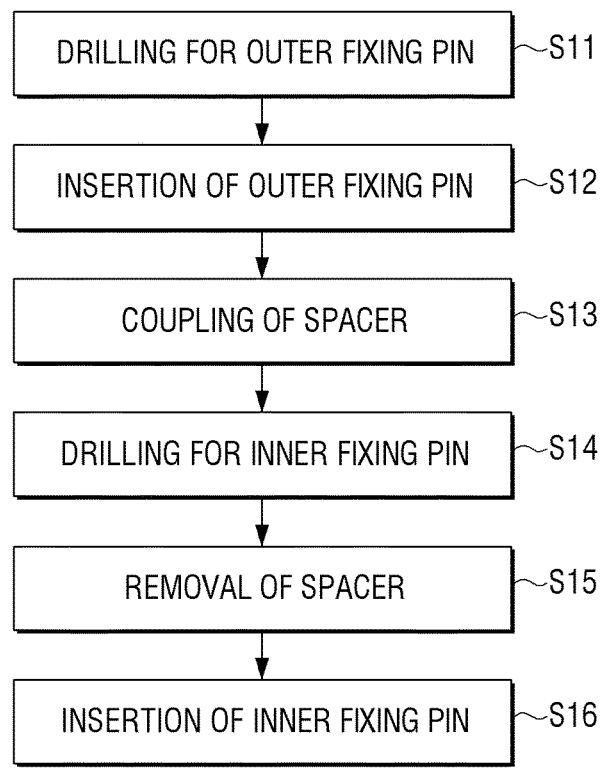
FIG. 6 is a flow chart illustrating a method of using a spacer as another example of a method of inserting an inner fixing pin and an outer fixing pin of FIG. 1.

As another example of the method of inserting the inner fixing pin 10 and the outer fixing pin 20, a spacer 70 may be used. A flow chart related to this method is illustrated in FIG. 6, and sequence views related thereto are illustrated in FIGS. 7A to 7F.

Figure 7A:
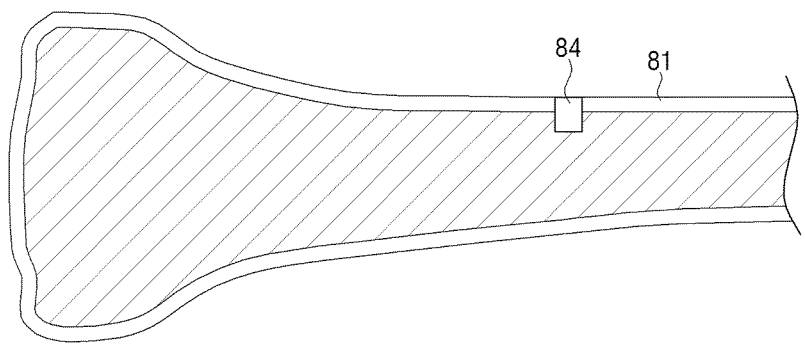
FIGS. 7A to 7F are sequence views illustrating the method of using the spacer as another example of the method of inserting the inner fixing pin and the outer fixing pin of FIG. 1.

In order to specifically describe another example, first, referring to FIG. 7A, drilling for inserting the outer fixing pin 20 is performed on one-side cortex 81, thereby forming the hole 84 for inserting the outer fixing pin 20 (S11). In this case, it is preferable that the drilling is performed so as to form a screw thread in the cortex for coupling with the first screw portion 21 of the outer fixing pin 20.

Figure 7B:
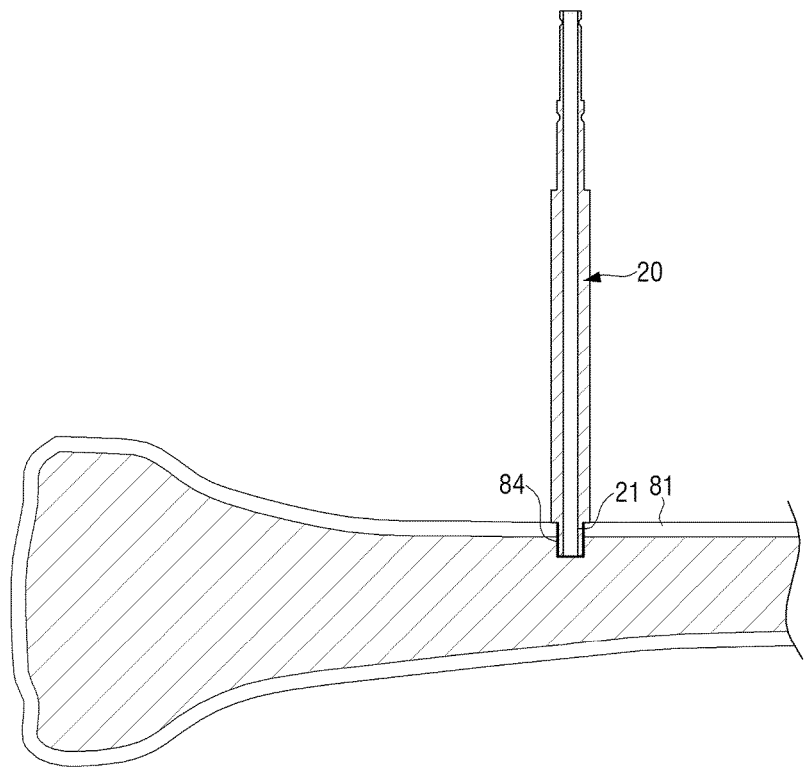

Then, referring to FIG. 7B, the outer fixing pin 20 is inserted into the hole 84 for inserting the outer fixing pin 20, formed in one-side cortex 81 (S12). The outer fixing pin 20 is screw-coupled to the hole 84 for inserting the outer fixing pin 20, formed in one-side cortex along the first screw portion 21 formed on the front of the outer fixing pin 20.

Figure 7C:
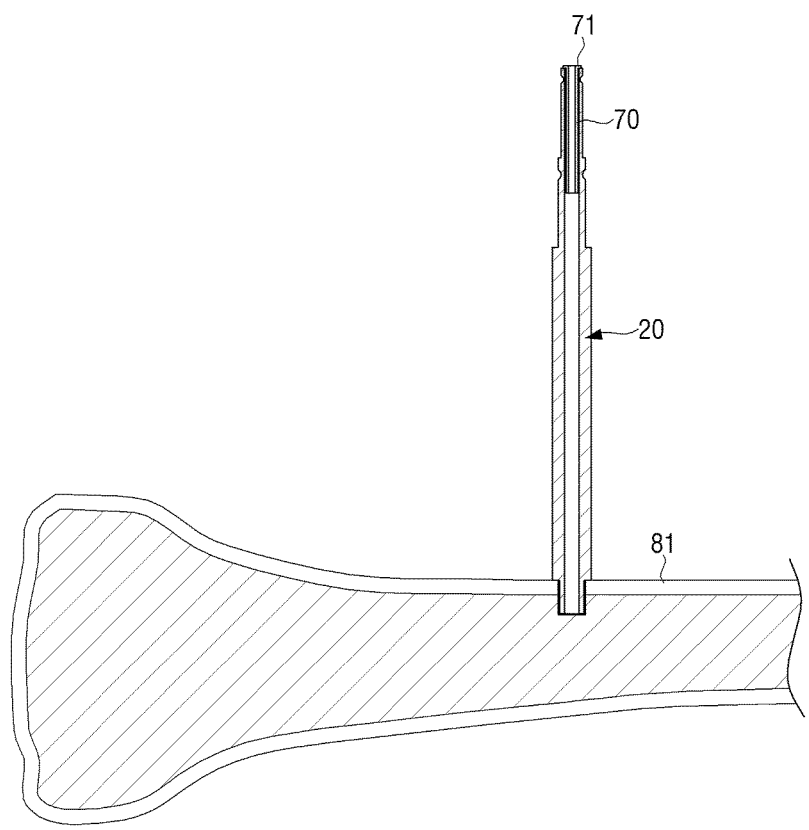

Then, referring to FIG. 7C, the spacer 70 is inserted into the first hole 24 at the rear end of the outer fixing pin 20 (S13). The spacer 70, which is a member for guiding the drilling in order to insert the inner fixing pin 10 into an accurate position, has a bar shape with a size corresponding to the size of the first hole 24 of the outer fixing pin 20. Further, a hole is formed in the spacer 70 so that the drilling may be preformed, and a catching member 71 caught by the rear end of the outer fixing pin 20 so as not to be further inserted is formed at a rear end of the spacer 70.

Figure 7D:
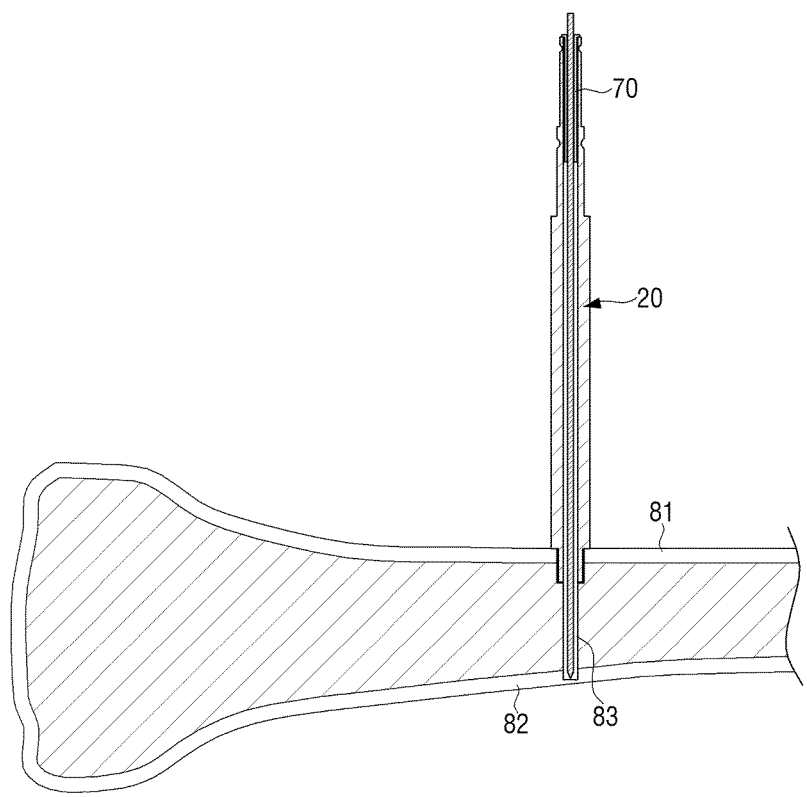

Next, referring to FIG. 7D, drilling for forming the hole 83 for inserting the inner fixing pin 10 is performed according to guide of the spacer 70 (S14). Since the inner fixing pin 10 needs to be inserted up to the opposite-side cortex, the drilling is performed up to the opposite-side cortex 82.

Figure 7E:
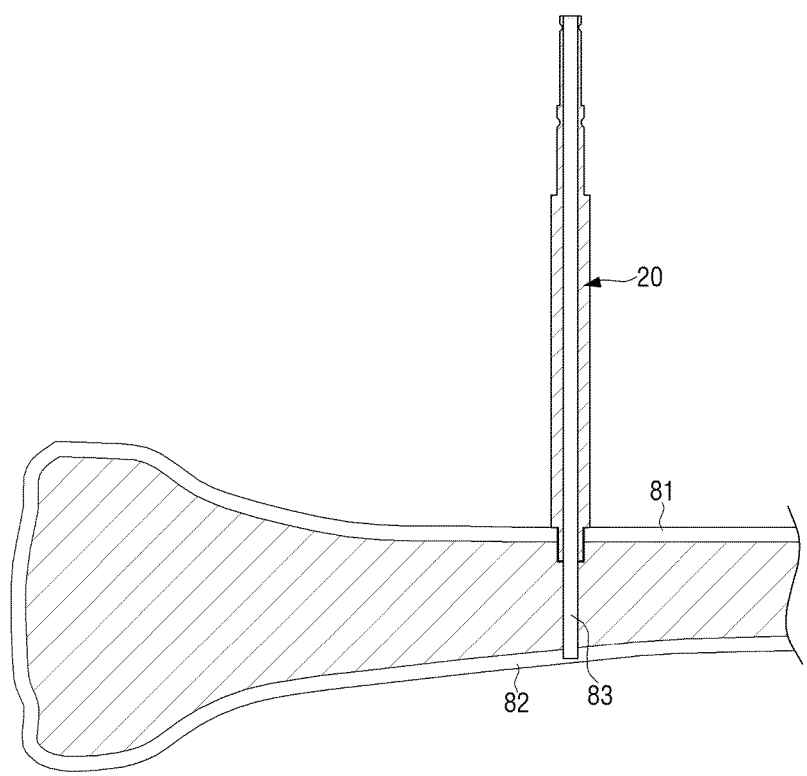
Figure 7F:
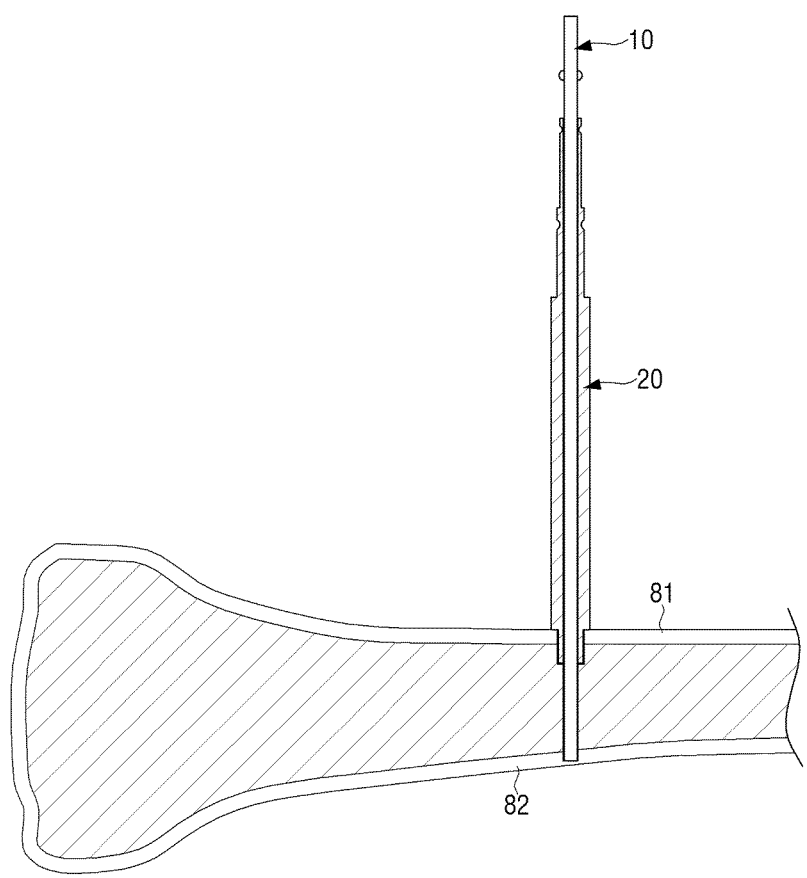

Then, referring to FIG. 7E, the spacer 70 is removed (S15). Next, as illustrated in FIG. 7F, the inner fixing pin 10 is inserted (S16).

Thereafter, a method of coupling the fixing nut 40 and the stopper 50 and a method of treating bone fracture using the fixing pin 1 are the same as described above, a description thereof will be omitted.

At the time of inserting the inner fixing pin 10 using the spacer 70, there is an advantage in that the inner fixing pin 10 may be inserted into a more accurate position as compared to the case in which the spacer 70 is not used.

Figure 8A:
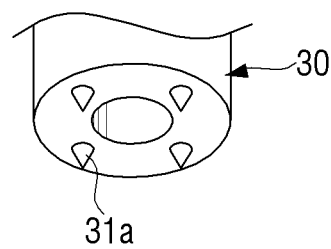
FIGS. 8A to 8F are partially perspective views illustrating various examples of a spike formed at a front end of a sleeve illustrated in FIG. 1.
Figure 8B:
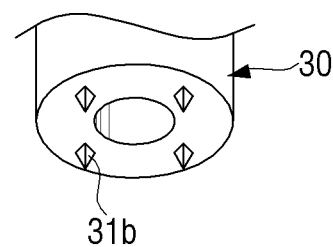
Figure 8C:
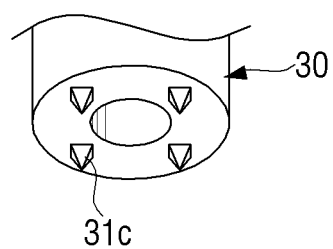
Figure 8D:
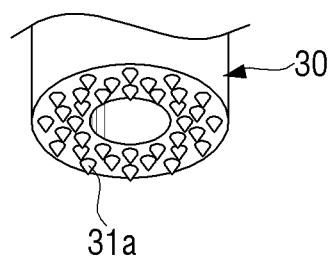

Referring to FIGS. 8A to 8D, a plurality of spikes 31a, 31b, and 31c having at least one shape of a corn, a triangular pyramid, and a quadrangular pyramid may be formed in the front of the sleeve 30 in order to obtain strong fixation force with the bone. The plurality of spikes 31a, 31b, and 31c may be provided along an outer portion of the front end of the sleeve 30. Alternatively, the plurality of spikes may be densely provided at the front end of the sleeve 30 in order to further increase fixation force between the sleeve 30 and the bone as illustrated in FIG. 8D. The spike as described above allows the fixing pin to be strongly fixed to the bone at the time of reposition of bone fracture, thereby performing reposition of the bone at the accurate position.

Figure 8E:
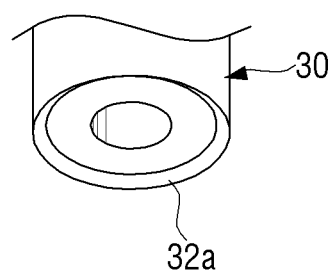
Figure 8F:
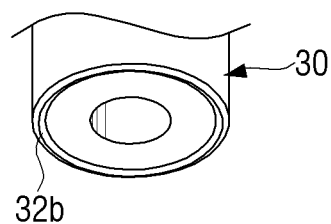

Referring to FIGS. 8E and 8F, as another example of the sleeve 30, a spike 32a or 32b may be formed to continuously protrude from the front end. In this case, the continuous spike 32a or 32b is formed at the front end of the sleeve 30, thereby forming strong fixation force between the sleeve 30 and the bone.

Figure 9:
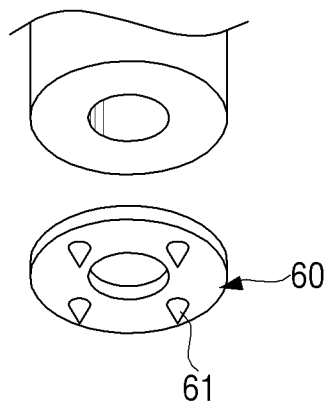
FIG. 9 is a partially perspective view illustrating a washer inserted on the front end of the sleeve illustrated in FIG. 1.

Referring to FIG. 9, as another example for forming strong fixation force between the sleeve 30 and the bone, a washer 60 inserted between the front end of the sleeve 30 and the bone is illustrated. A spike 61 is formed at a portion of the washer 60 contacting the bone, similarly to the front end of the sleeve 30. The spike 61 of the portion of the washer 60 contacting the bone may be formed in the same shape as that of the spike 31a, 31b, 31c, 32a, or 32b formed at the front end of the sleeve 30 described above. That is, a plurality of spikes having at least one shape of a corn, a triangular pyramid, and a quadrangular pyramid may be formed. As another example, the spike may be formed to continuously protrude at the portion of the washer 60 contacting the bone.

As described above, in the case of using the fixing pin for orthopedic surgery according to the present disclosure, it is possible to minimize incision in a surgical site, such that secondary infection in the surgical site may be prevented, which assists in recovery of a patient. Further, due to strong fixation force of the sleeve 30, it is possible to perform accurate reposition of bone fracture. The fixing pin for orthopedic surgery as described above may replace an existing fixing pin used in internal fixation, and will contribute to robotic surgery era in the future.

The present disclosure is not limited to the exemplary embodiments described above, but simple substitution, addition, deletion, and modification of components which may be performed by those skilled in the art, without departing from the scope and spirit of the disclosure as disclosed in the accompanying claims should also be understood to fall within the scope of the present disclosure.

INDUSTRIAL APPLICABILITY

The present disclosure relates to a fixing pin for orthopedic surgery capable of solving a problem that it is impossible to perform internal fixation in the case of performing reposition of bone fracture using a fixing pin, and capable of improving accuracy and safety of musculoskeletal reconstruction surgery of damaged upper and lower extremities.

What is claimed is:

1. A fixing pin for orthopedic surgery comprising:
an inner fixing pin configured to be inserted from one-side cortex of a bone to the opposite-side cortex thereof;
an outer fixing pin including a first hole and a first screw portion formed to protrude from a front end thereof, the first hole being penetrated by the inner fixing pin so that front and rear ends of the inner fixing pin protrude; and
a stopper fixing the inner fixing pin to the outer fixing pin, the first screw portion of the outer fixing pin being inserted into only one-side cortex of the bone, and
the inner fixing pin being fixed to the outer fixing pin, wherein the outer fixing pin has a larger outer diameter than an outer diameter of the first screw portion of the outer fixing pin such that only the first screw portion of the outer fixing pin is insertable into the bone, and
wherein the stopper includes a first coupling groove and a first coupling protrusion,
the first coupling groove being coupled to a second coupling protrusion of the inner fixing pin, and
the first coupling protrusion being coupled to a second coupling groove of the outer fixing pin and including a switch portion for coupling or separating the stopper to or from the outer fixing pin.

2. The fixing pin for orthopedic surgery as claimed in claim 1, further comprising a sleeve including a second hole and fixed to the outer fixing pin, the second hole being penetrated by the outer fixing pin so that front and rear ends of the outer fixing pin protrude.

3. The fixing pin for orthopedic surgery as claimed in claim 2, further comprising a fixing nut fixing the sleeve to the outer fixing pin.

4. The fixing pin for orthopedic surgery as claimed in claim 3, wherein the fixing nut is screw-coupled to a second screw portion formed at a middle portion of the outer fixing pin to fix the sleeve so that the sleeve is not separated from the outer fixing pin.

5. The fixing pin for orthopedic surgery as claimed in claim 2, wherein the sleeve includes a plurality of spikes having at least one shape of a corn, a triangular pyramid, and a quadrangular pyramid at a front end thereof.

6. The fixing pin for orthopedic surgery as claimed in claim 2, wherein a spike is formed to continuously protrude from a front end of the sleeve.

7. The fixing pin for orthopedic surgery as claimed in claim 2, wherein the sleeve includes a washer inserted on the front end thereof, the washer including a plurality of spikes having at least one shape of a corn, a triangular pyramid, and a quadrangular pyramid on one surface thereof.

8. The fixing pin for orthopedic surgery as claimed in claim 2, wherein the sleeve includes a washer inserted on the front end thereof, the washer including a spike formed to continuously protrude from a front end of the washer.

9. The fixing pin for orthopedic surgery as claimed in claim 1, further comprising a spacer disposed between the inner fixing pin and the outer fixing pin in order to insert the inner fixing pin at an accurate position, and including a hole penetrated by the inner fixing pin.

* * * * *